US011554128B2

(12) United States Patent
Duroux et al.

(10) Patent No.: US 11,554,128 B2
(45) Date of Patent: Jan. 17, 2023

(54) PHYTATES FOR USE AS A BIOMOLECULES DELIVERY OR ADSORPTION SYSTEM

(71) Applicant: Croda International Plc, Goole (GB)

(72) Inventors: Laurent Duroux, Bronshoj (DK); Erik Lindblad, Frederiksberg (DK)

(73) Assignee: Croda International Plc, Goole (GB)

( * ) Notice: Subject to any disclaimer, the term of this patent is extended or adjusted under 35 U.S.C. 154(b) by 0 days.

(21) Appl. No.: 17/044,768

(22) PCT Filed: Apr. 10, 2019

(86) PCT No.: PCT/EP2019/059078
§ 371 (c)(1),
(2) Date: Oct. 1, 2020

(87) PCT Pub. No.: WO2019/201701
PCT Pub. Date: Oct. 24, 2019

(65) Prior Publication Data
US 2021/0106598 A1  Apr. 15, 2021

(30) Foreign Application Priority Data
Apr. 16, 2018 (EP) .................... 18167427

(51) Int. Cl.
*A61K 31/6615* (2006.01)
*A61K 9/14* (2006.01)
*A61K 33/06* (2006.01)
*A61K 39/39* (2006.01)

(52) U.S. Cl.
CPC .......... *A61K 31/6615* (2013.01); *A61K 9/145* (2013.01); *A61K 33/06* (2013.01); *A61K 39/39* (2013.01)

(58) Field of Classification Search
CPC .... A61K 31/6615; A61K 9/145; A61K 33/06; A61K 39/39; A61K 2039/55505
See application file for complete search history.

(56) References Cited

U.S. PATENT DOCUMENTS

2010/0143385 A1* 6/2010 Cook ............... A61P 13/12
424/175.1
2017/0216191 A1* 8/2017 Deisenroth .......... A61K 8/4926

FOREIGN PATENT DOCUMENTS

EP  3162376 A1  3/2017
WO 2005023176 A2  3/2005

OTHER PUBLICATIONS

Tung, M. S., et al Carries Res. vol. 19, pp. 72-75, 1985.*
Li et al., "Aluminum hydroxide nanoparticles show a stronger vaccine adjuvant activity than traditional aluminum hydroxide micro-particles", J. Control. Release, Jan. 10, 2014, 173, pp. 148-157.
Li et al., "Peptide vaccine: progress and challenges", Vaccines, 2014, 2(3), 515-536.
Woods et al., "Amazing stability of the arginine-phosphate electrostatic interaction", Journal of Proteome Research, 2005, 4(4), pp. 1397-1402.
International Search Report and Written Opinion for International Application PCT/EP2019/059078, dated Jul. 8, 2019, 11 pages.
Coursaget et al., "Clinical trial of hepatitis B vaccine in a simplified immunization programme", Bulletin of the World Health Organization, 64 (6), 1986, pp. 867-871.
Fokkens et al., "A molecular tweezer for lysine and arginine", Journal of the American Chemical Society, 2005, 7 pages.
Ganesan et al., "Calcium phosphate nanoparticles as nuclei for the preparation of colloidal calcium phytate", New Journal of Chemistry, Jan. 1, 2008, vol. 32, No. 8, 5 pages.
Higashi et al., "Particle size of tin and phytate colloid in sentinel node identification1", Journal of Surgical Research, vol. 121, No. 1, Sep. 1, 2004 (Sep. 1, 2004), pp. 1-4.
Lindblad, E., "Aluminum compounds for use in vaccines", Immunology and Cell Biology, 2004,82, pp. 497-505.
Mavri et al., "Ion pair formation of phosphorylated amino acids and lysine and arginine side chains: A theoretical study", Proteins: Structure, Function and Genetics, 24, 1996, pp. 495-501.
Morefield et al., "Role of aluminum-containing adjuvants in antigen internalization by dendritic cells in vitro", Vaccine, 23, 2005, pp. 1588-1595.
Relyveld et al., "Simultaneous Administration of Diphtheria-Tetanus-Pertussis-Polio and Hepatitis B Vaccines in a Simplified Immunization Program: Immune Response to Diphtheria Toxoid, Tetanus Toxoid, Pertussis, and Hepatitis B Surface Antigen", Infection and Immunity, Mar. 1986, pp. 784-787.
Relyveld et al., "Humoral response in rabbits immunized with calcium phosphate adjuvanted HIV-1 gp160 antigen", Biomed & Pharmacother, 48, 1994, pp. 79-83.
Schug et al., "Noncovalent binding between guanidinium and anionic groups: focus on biological-and synthetic-based arginine/guanidinium interactions with phosph[on]ate and sulf[on]ate residues", Chemical Reviews, 105 2005, pp. 67-113.
Vasilev et al., "Magnetic Properties of the Mn1+xSb1-xSnx Systems", Phys. Stat. Sol., (a) 47, K55, 1978, 3 pages.

* cited by examiner

*Primary Examiner* — Gollamudi S Kishore
(74) *Attorney, Agent, or Firm* — RatnerPrestia

(57) ABSTRACT

The present invention relates to mineral micro-particles comprising phytate (inositol hexaphosphate, IP6). More particularly, the invention provides salts of phytic acid with multivalent metal ions such as $Ca^{2+}$ and $Mg^{2+}$ for use in biomolecules delivery or adsorption systems, methods for their production and uses thereof, such as for use as a vaccine adjuvant.

8 Claims, 2 Drawing Sheets

PHYTATES FOR USE AS A BIOMOLECULES DELIVERY OR ADSORPTION SYSTEM

CROSS REFERENCE TO RELATED APPLICATIONS

This application is the National Stage filing of International Application No. PCT/EP2019/059078, filed Apr. 10, 2019, and claims priority to EP 18167427.6, filed Apr. 16, 2018, both of which are incorporated herein by reference for all purposes.

TECHNICAL FIELD

The present invention relates to mineral micro-particles comprising phytate and one or more multivalent cations $M^{2+}$, $M^{3+}$ or organic polycations. More particularly, the invention provides such mineral micro-particles for use in biomolecules delivery or adsorption systems, such as for use as vaccine adjuvants.

BACKGROUND OF THE INVENTION

Mineral adjuvants, such as aluminum-containing adjuvants, including aluminum phosphate, aluminum hydroxide and calcium phosphate, have been used successfully for decades to enhance the immune response against killed, inactivated and subunit vaccine antigens.

Aluminum adjuvants are, at present, the most widely used adjuvants in both veterinary and human vaccines. Calcium phosphate has so far only been used to a limited extent as an adjuvant in commercial veterinary vaccines, but has been used as an adjuvant in vaccines against diphtheria, tetanus, *Bordetella pertussis* and poliomyelitis (Relyveld, 1986; Coursaget et al., 1986), commercialised by Institut Pasteur. Calcium phosphate was also used as an adjuvant in the IPAD series of vaccines by Institut Pasteur for approx. 25 years. Further, calcium phosphate has been tested as an adjuvant in experimental vaccines with the gp160 antigen from HIV (Relyveld and Chermann, 1994).

Both aluminum hydroxide and calcium phosphate have been used as adjuvants in commercialised adsorbed allergen preparations for hyposensitization of allergic patients (Relyveld et al., 1985). This application is particularly interesting, partly because allergic patients develop antigen-specific IgE type antibodies, which can lead to mast cell degranulation and anaphylaxia.

With the calcium phosphate adjuvant, the literature data suggest that this adjuvant does not give lead to significant stimulation of IgE antibodies. Vassilev (Vassilev, 1978) compared to the reaction in terms of passive cutaneous anaphylaxis (PCA) in guinea pigs after two immunizations with either aluminum or calcium phosphate adjuvant using tetanus toxoid as antigen. It was found that calcium phosphate treated guinea pigs only had insignificant IgE titres compared to the group that had received Al-adjuvanted vaccines. The research in this field is however sparse and there are at present no data on the interleukin profile after immunization with calcium phosphate to illustrate possible underlying differences in the mechanisms behind such a difference.

A major difference between aluminum- and calcium-based adjuvants lies in the clearing in vivo of the adjuvant inoculum and the metabolic fate of the degradation products. Upon degradation of calcium phosphate, its two constituents can be re-utilized in the normal metabolic pathways for $Ca^{2+}$ and $PO_4^{3-}$ respectively, whereas in contrast to other metallic ions, like $Zn^{2+}$ and $Mg^{2+}$, aluminum does apparently not act as essential trace element or co-enzyme in the normal metabolism.

The strength and the nature of binding of the antigen to the adjuvant is another important parameter as it conditions the probability for the antigen to be presented in particulate form (bound to adjuvant particles) instead of being released in free form into the surrounding physiological environment. This might be particularly relevant for small soluble peptides with high diffusion constants, as a matter of fact peptides as vaccines are generally known to elicit poor immunogenicity and need to be adjuvanted (Li, W., Joshi, M. D., Singhania, S., Ramsey, K. H., & Murthy, A. K. (2014). Peptide vaccine: progress and challenges. Vaccines, 2(3), 515-536.].

Another aspect of the adjuvant potency might be related to particle size. For example, it has been shown by Morefield et al. (Morefield G. L. et al., Role of aluminum-containing adjuvants in antigen internalization by dendritic cells in vitro, Vaccine, 2005) and Li et al. (Li X. et al., Aluminum hydroxide nanoparticles show a stronger vaccine adjuvant activity than traditional aluminum hydroxide micro-particles, J. Control. Release, 2014) that smaller-sized aluminum-containing particles perform better compared to larger particles, in particular for inducing antigen-specific antibody responses, as smaller particles can be transported to the nearest afferent lymph nodes.

There is therefore a need for developing alternative adjuvants, which ideally should incur neglible side effects, have optimal particle size and antigen binding strength, and allow high doses of antigen per units of adjuvants. This would potentially allow for a reduction of the adjuvant loads for the same dose of antigen, leading to reduced costs of manufacturing.

SUMMARY OF THE INVENTION

The present inventors have found that mineral microparticles comprising one or more phytic acid (IP6) salts comprising multivalent cations $M^{2+}$ and $M^{3+}$ or organic polycations for use as biomolecules delivery or adsorption systems and that these IP6-M microparticles have comparable or improved antigen binding properties compared to aluminum hydroxy-phosphate adjuvant particles.

Phytic acid (inositol hexaphosphat, IP6) is a phosphoric acid ester of inositol, in which each of the six hydroxyl groups in inositol has been esterified with a molecule of orthophosphoric acid. Since orthophosphoric acid is a tribasic acid and since only one hydrogen is affected in the esterification of inositol, each molecule of phosphoric acid is still functional as a dibasic acid. Since there are six of these phosphoric acid molecules now associated with inositol in the ester, the ester functions as a dodecabasic acid. As such, phytic acid is capable of forming salts in which metallic and other positive ions may replace hydrogen in the acid in varying degrees, up to the limit of replacing all twelve hydrogen atoms. For phytic acid (Phy) precipitating with divalent metal (M) ions, the theoretical limit is thus $PhyM_6$. However, if the divalent metal ions co-precipitate with other anions, the phytic acid salt may contain more than 6 divalent metal ions pr molecule phytic acid, such as $PhyM_7X$ or $PhyM_8X_2$.

Phytic acid has previously been shown to form insoluble salts with multivalent cations (e.g. $M^{2+}$ and $M^{3+}$) as well as organic polycations. These insoluble salts form particulate matter, which have been found by the present inventors to be possible alternatives to the classical aluminum salt particles presently used as adjuvants.

The mineral microparticles of the present invention thus show negative zeta-potentials comparable or larger than those measured for aluminum hydroxy-phosphate adjuvant particles. This indicates that IP6-M particles are well-suited for the adsorption of positively charged antigens or immunopotentiators.

The phytic acid salts in the context of the present invention may comprise one or more different multivalent metal (M) cations, such as, for example, $Ca^{2+}$, $Mg^{2+}$ or both $Ca^{2+}$ and $Mg^{2+}$. The phytic acid salts may also comprise one or more organic polycations such as, for example, poly-L-lysine and/or deacylated poly-D-glucosamine (aka chitosan). Compositions comprising phytic acid salts according to the present invention, such as adjuvant compositions, may also contain more than phytic acid salt.

One advantage of phytic acid is its capacity to tolerate heat sterilization, which is required for the manufacture of vaccines. The phospho-ester bonds between phosphate groups and the alcohols of inositol are resistant to hydrolysis during autoclaving conditions used for the manufacture of such adjuvants, releasing only a fraction of free orthophosphate and inositol phosphates.

Additionally, the present inventors have found that the mineral micro-particles of the present invention have increased binding properties for positively-charged biomolecules, or biomolecules with patches of positive charges, more particularly antigen-binding properties. This property is presumably caused by an increased attraction of positively-charged biomolecules, such as antigens, to the surface of said mineral micro-particles, leading to an increased adsorption capacity and/or binding strength, i.e. an increased association constant. In view hereof, the modified mineral micro-particles according to present invention can, for instance, be used as improved vaccine adjuvants.

In a first aspect there is therefore provided mineral microparticles comprising one or more phytic acid (IP6) salts comprising multivalent cations $M^{2+}$ and $M^{3+}$ or organic polycations for use as biomolecules delivery or adsorption systems, in particular as vaccine adjuvants.

In a second aspect there is provided a manufacturing method for the mineral microparticles according to the first aspect.

In a third aspect there are provided mineral micro-particles which are obtainable by the manufacturing method according to the first aspect.

In a fourth aspect there are provided adjuvant compositions comprising mineral microparticles according to the first aspect.

In a fifth aspect adjuvant compositions according to the third aspect are combined with one or more antigens to form vaccine compositions.

DEFINITIONS

Figure 1:
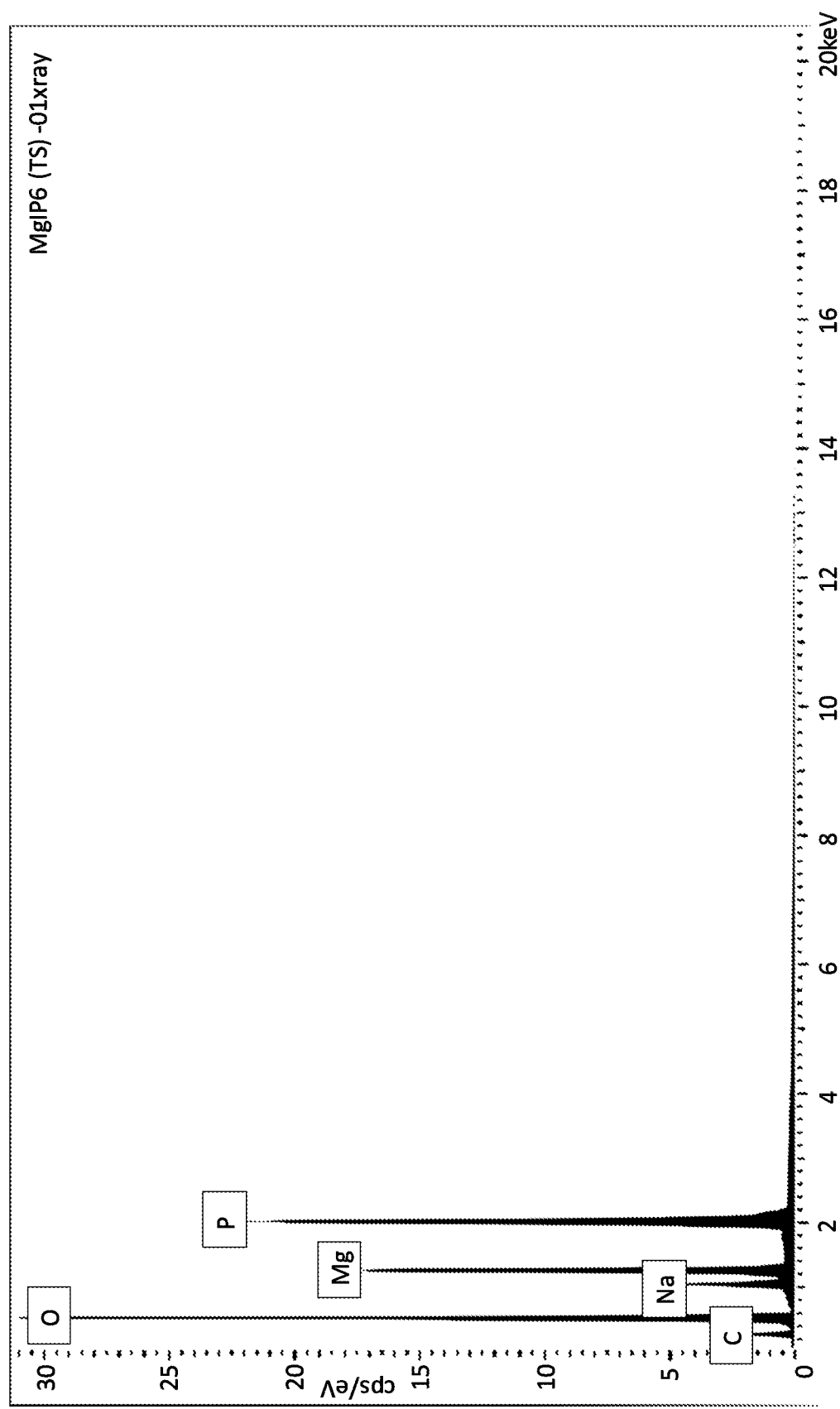
FIG. 1. EDXS spectrum of K-shell energies for IP6-Mg precipitate.
Figure 2:
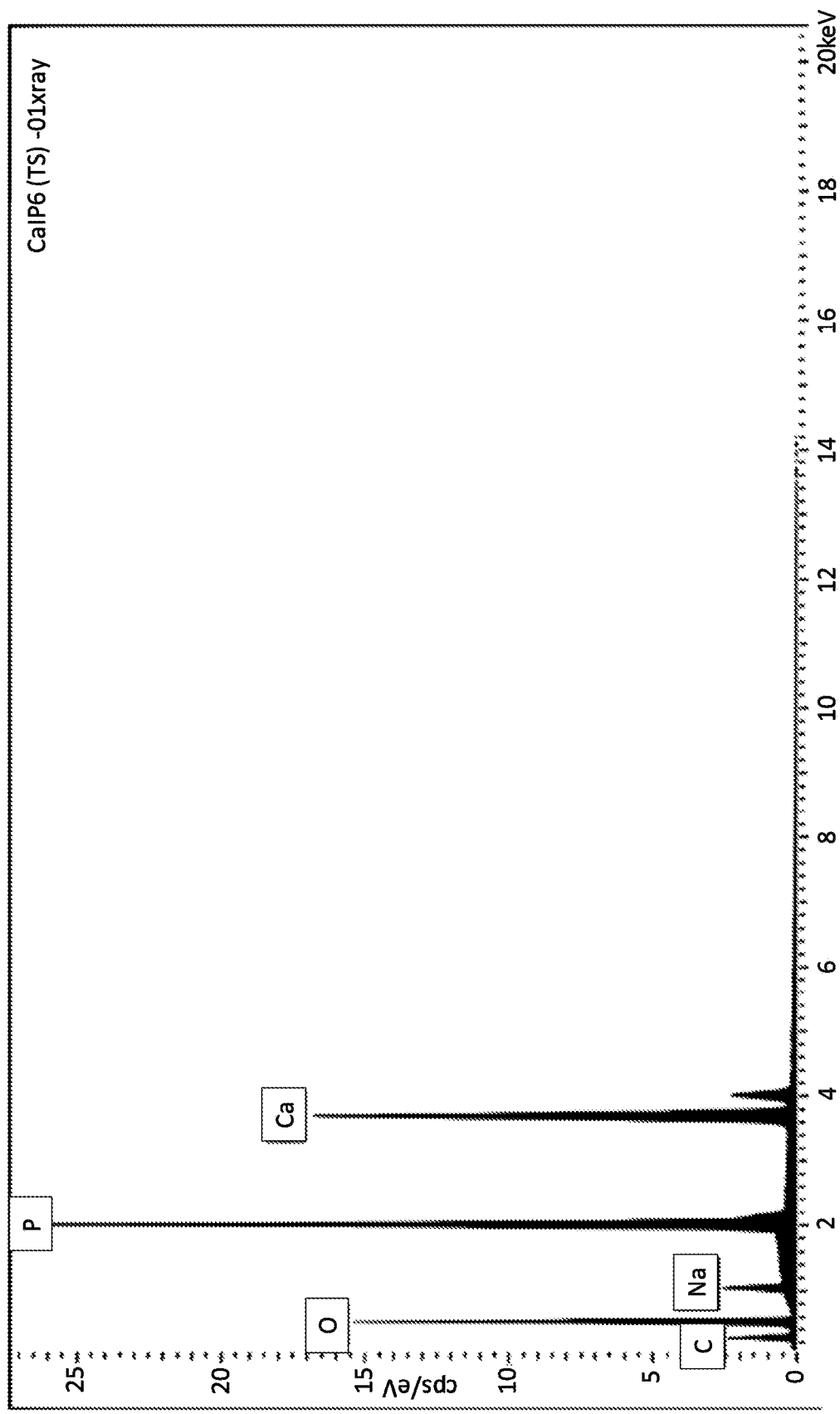
FIG. 2. EDXS spectrum of K-shell energies for IP6-Ca precipitate.

Unless defined otherwise, all technical and scientific terms used herein have the same meaning as commonly understood by one of ordinary skill in the art to which this invention belongs. Although any methods and materials similar or equivalent to those described herein may be used in the practice of testing of the present invention, the preferred methods and materials are now described.

In this specification and the appended claims, the singular forms "a", "an", and "the" include plural references unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps.

The terms "comprising", "comprises" and "comprised of" also include the term "consisting of".

The term "about" as used herein when referring to a measurable value such as a parameter, an amount, a temporal duration, and the like, is meant to encompass variations of +/−10% or less, preferably +/−5% or less, more preferably +/−1% or less, and still more preferably +/−0.1% or less of and from the specified value, insofar such variations are appropriate to perform in the disclosed invention. It is to be understood that the value to which the modifier "about" refers is itself also specifically, and preferably, disclosed.

The recitation of numerical ranges by endpoints includes all numbers and fractions subsumed within the respective ranges, as well as the recited endpoints.

In the following passages, different aspects or embodiments of the invention are defined in more detail. Each aspect or embodiment so defined may be combined with any other aspect(s) or embodiment(s) unless clearly indicated to the contrary. In particular, any feature indicated as being preferred or advantageous may be combined with any other feature or features indicated as being preferred or advantageous.

Reference throughout this specification to "one embodiment", "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments.

In the context of the present application, "M" denotes a metal atom, and $M^{2+}$ and $M^{3+}$ denote examples of di- and trivalent metal cations.

DETAILED DESCRIPTION OF THE INVENTION

The present invention relates to mineral microparticles comprising one or more phytic acid (IP6) salts comprising multivalent metal cations $M^{2+}$, $M^{3+}$ or organic polycations. It has been found that the biomolecule-binding properties, preferably when said biomolecule is a vaccine antigen, of these phytate-containing mineral micro-particles are comparable or improved vis-à-vis typical phosphate-containing mineral micro-particles. In particular, it was shown that the (formal) substitution of phosphate ions or hydroxide ions by phytate ions increased the numerical value of the ζ-(zeta-) potential of said micro-particles, thereby increasing the strength of the electrostatic potential, e.g. for attraction of biomolecules, preferably antigens, and/or the binding strength to the surface of said micro-particles.

The mineral microparticles of the present invention thus show negative zeta-potentials similar or numerically larger than those measured for aluminum hydroxy-phosphate adjuvant particles, which strongly indicates that IP6-M particles are well-suited for the adsorption of positively charged antigens or immunopotentiators.

Phytic acid (inositol hexaphosphate, IP-6) has previously been shown to form practically insoluble salts with multivalent cations (e.g. $M^{2+}$ and $M^{3+}$) as well as with organic polycations. These insoluble salts were hypothesized by the present inventors to be alternatives to the classical aluminum salt particles presently used as adjuvants.

One advantage of employing phytic acid salts as adjuvants is its heat stabilty and tolerance towards heat sterilization, which is required for the manufacture of vaccines. The phospho-ester bonds between phosphate groups and the hydroxy groups of inositol are resistant to hydrolysis during autoclaving conditions used for the manufacture of such adjuvants, releasing only a fraction of free orthophosphate and inositol phosphates.

The phytic acid salts in the context of the present invention may comprise one or more different multivalent metal (M) cations, such as, for example, $Ca^{2+}$, $Mg^{2+}$ or both $Ca^{2+}$ and $Mg^{2+}$. The phytic acid salts may also comprise one or more organic polycations such as, for example, poly-L-lysine and/or deacylated poly-D-glucosamine (aka chitosan). Compositions comprising phytic acid salts according to the present invention may also contain more than one phytic acid salt.

In a first aspect there is therefore provided mineral microparticles comprising one or more phytic acid (IP6) salts comprising multivalent cations $M^{2+}$ and $M^{3+}$ or organic poly-cations for use as biomolecules delivery or adsorption systems.

In an embodiment, said multivalent cations are divalent alkaline earth metal ions.

In an embodiment, said multivalent cations are organic polycations.

In another embodiment said organic polycations are selected from poly-L-lysine and/or deacylated poly-D-glucosamine (aka chitosan).

In another embodiment said divalent alkaline earth metal ions are selected from $Ca^{2+}$ and $Mg^{2+}$ or mixtures thereof.

In a specific embodiment, said mineral microparticles are calcium phytate microparticles.

In another specific embodiment, said mineral microparticles are magnesium phytate microparticles.

In another embodiment the mineral microparticles of the present invention comprise at least one other anion than phytate.

In a preferred embodiment, the mineral microparticles of the present invention are useful as vaccine adjuvants.

Another advantage of the present invention lies in the large number of possible combinations of phytate with multivalent cations and mixtures thereof, which may be formed in different stoichiometric ratios as phytic acid has 6 phosphate groups which can interact with one, two, or more identical or different multivalent cations. The resulting mineral microparticles may further be precipitated or post-processed in different particle sizes. The mineral microparticles of the present invention can thus be tailor-made as biomolecules delivery or adsorption systems to be ideally matched as adjuvants for different antigens.

In a second aspect there is provided a manufacturing method for the mineral microparticles according to the first aspect which comprises mixing phytic acid (IP6) or a soluble salt thereof with either a soluble salt of a multivalent cation, such as a soluble salt of a divalent alkaline earth metal ions like $CaCl_2$ or $MgCl_2$ or with a soluble organic cation like poly-L-lysine. The resulting precipitate is isolated, for example by centrifugation or filtration, and rinsed with deionised water.

The micro-particles according to the second aspect of the present invention are difficult to describe in exact, objective terms as the resulting precipitates do not necessarily have a composition matching a theoretical stoichiometric ratio. Furthermore, small changes in reaction conditions may affect the crystallinity and/or particle size of the microparticles. However, experience shows that mineral microparticles are repeatedly obtained with substantially identical performance/zeta-potential by following the procedure described. The mineral micro-particles are thus most precisely described as the product of said manufacturing method described herein.

In a third aspect there are thus provided mineral microparticles which are obtainable by the manufacturing method according to the second aspect.

In a fourth aspect there are provided adjuvant compositions comprising mineral microparticles according to the first or third aspect.

In an embodiment said adjuvant compositions comprise divalent alkaline earth metal ions.

In another embodiment said adjuvant compositions comprise alkaline earth metal ions selected from $Ca^{2+}$ and $Mg^{2+}$ or mixtures thereof.

In a specific embodiment said adjuvant compositions comprise calcium phytate microparticles.

In particular embodiments, the mineral micro-particles as taught herein may have increased antigen adsorption capacities as a result of their increased antigen-binding capacities. These increased antigen adsorption capacities will make it possible to make combination vaccines that may contain antigens from a higher number of infectious agents compared to what is available in the prior art. The protein adsorption capacities of an adjuvant can be measured using a variety of analytical methods. For example, by comparing the protein content in the aqueous phase of the antigen solution before and after adsorption onto the adjuvant (Lindblad E., Aluminum compounds for use in vaccines, Immunology and Cell Biology, 2004,82:497-505), or in case that an antibody specific for the desired antigen is available, adsorption, the protein adsorption capacities can be measured using immunoprecipitation techniques, by using either quantitative immunoelectrophoresis or single radial immunodiffusion. Without the use of an antibody it can be tested by spectrophotometrically (Lindblad E., Aluminum compounds for use in vaccines, Immunology and Cell Biology, 2004,82:497-505).

In a fifth aspect adjuvant compositions according to the fourth aspect are combined with one or more antigens to form vaccine compositions.

The term "micro-particles" as used herein refers to particles with a nominal size of at least 0.01 μm and at most 10 μm, at most 5 μm, or at most 2 μm. Micro-particles according to the present invention preferably have a nominal size of 500 nm to 1 μm and a nominal ζ-potential as defined elsewhere in the specification. Micro-particles may have various shapes and may be, for example, spherical, conical, ellipsoid, complex-shaped, cylindrical or cubical. Furthermore, micro-particles in a collection of micro-particles may not have all the same size or shape.

The term "electrostatic potential", "electric potential" or "V" as used herein refers to the general meaning of this term as understood by the skilled person, and in particular the potential energy of a charged entity, such as a proton, an electron or an ion at a particular location near a molecule and may be defined as the energy per unit charge (q) (V=U/q). The electrostatic potential may be expressed in units of Joules/Coulomb, or Volts. The electrostatic potential may be used to predict and/or calculate the energies required to move charges from, for example, one potential $V_1$ to another potential $V_2$.

The term "zeta potential" or "ζ-potential" as used herein describes a measure of the relative electrical charge of micro-particles that are suspended in liquid. More particularly, ζ-potential refers to an intermediate electrical potential at a certain distance from a particle's physical surface, the boundary of the so-called diffuse layer (the so-called slipping plane), where ions are in equilibrium between the attractive electrostatic field of the particle surface and the surrounding liquid (e.g. solvent). Accordingly, the ζ-potential describes the electrical potential at a certain distance from a particle's physical surface where the charge of said particle does no longer interfere with the surrounding liquid. The ζ-potential typically ranges from +100 mV to −100 mV and can be measured by using the Zetasizer nano ZS (Malvern Instruments Inc.) in electro-kinetic mode, preferably at 25° C. and/or in deionized water. For micro-particles in a fluid applies that the higher the nominal ζ-potential, the higher the stability in terms of reduced tendency to settle when in suspension. For example, micro-particles with a ζ-potential greater than +25 mV or less than −25 mV typically have a high degree of stability.

The term "bind", "interact", "specifically bind" or "specifically interact" as used throughout this specification means that an agent binds to or influences one or more desired molecules or analytes substantially to the exclusion of other molecules which are random or unrelated, and optionally substantially to the exclusion of other molecules that are structurally related. The term "bind", "interact", "specifically bind" or "specifically interact" does not necessarily require that an agent binds exclusively to its intended target(s). For example, an agent may be said to specifically bind to target(s) of interest if its affinity for such intended target(s) under the conditions of binding is at least about 2-fold greater, preferably at least about 5-fold greater, more preferably at least about 10-fold greater, yet more preferably at least about 25-fold greater, still more preferably at least about 50-fold greater, and even more preferably at least about 100-fold greater, than its affinity for a non-target molecule.

The binding or interaction between the agent and its intended target(s) may be non-covalent (i.e., mediated by non-covalent forces, such as for example, ionic interactions, hydrogen bridges, dipolar interactions, van der Waals interactions, and the like). Preferably, the agent may bind to or interact with its intended target(s) with affinity or association constant ($K_A$) of such binding $K_A \geq 1 \times 10^6$ M$^{-1}$, more preferably $K_A \geq 1 \times 10^7$ M$^{-1}$, yet more preferably $K_A \geq 1 \times 10^8$ M$^{-1}$, even more preferably $K_A \geq 1 \times 10^9$ M$^{-1}$, and still more preferably $K_A \leq 1 \times 10^{10}$ M$^{-1}$ or $K_A \geq 1 \times 10^{11}$ M$^{-1}$, wherein KA= [A_T]/[A][T]=$k_a/k_d$, A denotes the agent, T denotes the intended target, $k_a$ denotes the rate of adsorption and $k_d$ denotes the rate of desorption. Determination of $K_A$ can be carried out by methods known in the art, such as for example, using equilibrium dialysis and Scatchard plot analysis.

Without wishing to be bound by any theory, the present inventors hypothesize that a second mechanism by which biomolecules, such as antigens, may bind to the surface of mineral micro-particles as taught herein is through more specific interactions involving the formation of ionic bonds between the positively charged amino acids at the protein surface of a biomolecule, preferably lysine and arginine, and the negatively charged phytic acid (IP6) phosphate groups at the surface of the micro-particles (e.g. adjuvant micro-particles). The affinity of phosphate groups for positively charged amino acids residues in proteins, especially lysine and arginine, is well documented in biochemistry, with the example of protein kinases and phosphatases where the phosphoryl group of nucleotides is transiently involved in ionic pairing with lysine or arginine residues of the enzyme catalytic site (Mavri J. and Vogel M. J., Ion pair formation of phosphorylated amino acids and lysine and arginine side chains: A theoretical study, Proteins Structure Function and Bioinformatics, 1996). In some particular cases of protein-protein interactions, it has been shown that this type of ionic bond can be as strong as a covalent bond (Woods A. S. and Ferré S., Amazing stability of the arginine-phosphate electrostatic interaction, Journal of Proteome Research, 2005), and this property is being exploited in some applications (Fokkens M. et al., A molecular tweezer for lysine and arginine, Journal of the American Chemical Society, 2005; Schug K. A. et al., Noncovalent binding between guanidinium and anionic groups: focus on biological- and synthetic-based arginine/guanidinium interactions with phosph[on]ate and sulf[on]ate residues, Chemical Reviews, 2005). The present inventors further hypothesize that this type of interaction can occur at the surface of phosphate containing micro-particles (e.g. used as adjuvants) such as the IP6-M microparticles taught herein, which comprise one or more phytic acid (IP6) salts comprising multivalent cations $M^{2+}$ and $M^{3+}$ or organic poly-cations, for use as biomolecules delivery or adsorption systems at appropriate pH values and ionic strength of the bulk solvent.

In particular embodiments, the mineral micro-particles as taught herein have:
 (i) a nominal ζ-potential of at least −28 mV, for IP6-Mg, when measured at pH 7.0 in distilled water, or
 (ii) a nominal ζ-potential of at least −34 mV, for IP6-Ca, when measured at pH 7.0 in distilled water.

In particular embodiments, the IP6-Mg micro-particles have a nominal ζ-potential of at least −20 mV, at least −25 mV, at least −30 mV or at least −35 mV when measured in distilled water, preferably at least −28 mV.

In particular embodiments, the IP6-Ca micro-particles have a nominal ζ-potential of at least −25 mV, at least −30 mV, at least −35 mV or at least −40 mV when measured in distilled water, preferably at least −34 mV.

In particular embodiments, the mineral micro-particles of the present invention have a nominal size of at least 0.1 μm and at most 2 μm, at least 0.5 μm and at most 2 μm, at least 0.5 μm and at most 1.5 μm, at most 1 μm, at most 0.5 μm, at most 0.2 μm, at most 0.1 μm, preferably between 0.5-1 μm.

The stoichiometric ratios of phytate/M for the micro-particles according to the invention are from about 1:3 to about 1:8, preferably 1:6 to 1:8, i.e. 6 to 8 M atoms per phytic acid molecule.

In particular embodiments, the IP6-Mg micro-particles according to the invention have a stoichiometric ratio phytate:Mg of 1:6.

In particular embodiments, the IP6-Ca micro-particles according to the invention have a stoichiometric ratio phytate:Ca of 1:8.

As noted above, mineral-containing adjuvants, including aluminum phosphate, aluminum hydroxide and calcium phosphate, have been used successfully in vaccine preparation for decades to enhance the immune response against killed, inactivated and subunit antigens.

In particular embodiments, the mineral micro-particles as taught herein which comprise one or more phytic acid (IP6) salts comprising multivalent cations $M^{2+}$ and $M^{3+}$ or organic poly-cations for use as biomolecules delivery or adsorption systems have increased biomolecule-binding properties compared to unmodified aluminum phosphate, amorphous aluminum hydroxyphosphate and/or calcium phosphate micro-particles, preferably wherein said biomolecule has an opposite charge than said modified micro-particle or wherein said biomolecule is neutral when said modified micro-particle is neutral. For example, modified aluminum phosphate micro-particles are negatively charged and preferably bind to positively charged biomolecules.

The term "biomolecules" as used herein is meant to include ingredients or agents that are derived from living organisms by purification or by synthesis and which may be biologically active. Also covered by these terms are diagnostic agents as well as so-called "cosmeceuticals". Diagnostic agents include, for example, fluorescent proteins (e.g. green fluorescent protein or GFP) or radiolabeled molecules. Cosmeceuticals include active ingredients that have an effect on the outer appearance of an individual such as on skin, hair, lips, and eyes, and encompass anti-wrinkling agents and agents that improve complexion. In these applications the modified micro-particles as taught herein preferably are administered externally. Active pharmaceutical ingredients (also referred to as medicinal products or drugs) are of particular interest and form a subgroup of biomolecules.

The biomolecules may include small molecules (such as those having a molecular weight of less than about 1,500), synthetic or natural such as monosaccharides, disaccharides, trisaccharides, oligosaccharides, peptides, nucleic acids but also nucleic acid analogues and derivatives; or large molecules, including plasmids, vectors, polysaccharides, biological macromolecules, e.g., larger peptides (polypeptides), proteins, peptide analogues and derivatives thereof, peptidomimetics, nucleic acid based molecules (e.g. DNA, RNA, mRNA, tRNA, RNAi, siRNA, microRNA, or any other DNA or RNA-like molecules), polynucleotides, oligonucleotides, enzymes, antibiotics, extracts made from biological materials such as bacteria, plants, fungi, or animal cells or tissues, therapeutic agents, preventatives, diagnostic agents, imaging agents, aptamers (including oligonucleotide or protein aptamers).

In one embodiment the biomolecules are water-soluble, particularly water-soluble active pharmaceutical ingredients. Such ingredients may belong to Class I or III of the Biopharmaceutical Classification System (BCS), which classifies drug substances into four classes: Class I—High Permeability, High Solubility; Class II—High Permeability, Low Solubility; Class III—Low Permeability, High Solubility; Class IV—Low Permeability, Low Solubility. Water-soluble drugs can also be specified by the amount of a water (g) required to solve 1 g of a compound, wherein water-soluble drugs are those fulfilling the following solubility qualifications: 10-30 g ("soluble"); 30-100 g ("sparingly soluble"); 100-1000 g ("slightly soluble"); 1000-10000 g ("very slightly soluble" or "poorly soluble"); or particularly soluble, sparingly soluble and slightly soluble drugs.

In another embodiment, the biomolecules may be antibodies or antibody fragments. The term "antibody" is meant to include monoclonal antibodies, polyclonal antibodies and multispecific antibodies (e.g. bispecific antibodies). Antibody fragments comprise a portion of an antibody, generally the antigen binding or variable region thereof. Examples of antibody fragments include Fab, Fab', $F(ab')_2$ and Fv fragments; diabodies; linear antibodies; single-chain antibody molecules; multispecific antibodies formed from antibody fragments.

In preferred embodiments, the biomolecules may be antigens which are capable of inducing an immune response in a host organism. Accordingly, in preferred embodiments, the mineral micro-particles as taught herein have increased antigen-binding properties compared to unmodified aluminum phosphate, amorphous aluminum hydroxyphosphate and/or calcium phosphate micro-particles, preferably wherein said antigen has an opposite charge than said modified micro-particle or wherein said antigen is neutral when said modified micro-particle is neutral. For example, modified aluminum phosphate micro-particles are negatively charged and preferably bind to positively charged antigens.

The term "host organism" typically denotes animals, preferably vertebrates, including birds, humans and non-human mammals, such as mice, rats, hamsters, guinea pigs, pigs, cows, horses, sheep, goats, dogs, cats or primates.

The term "adsorption" as used herein refers to physisorption (e.g. by van der Walls force) or chemisorption (e.g. by covalent or ionic bond) wherein the bond between the surface of the micro-particles and the biomolecule (e.g. antigen and/or organic molecule) is established.

In particular embodiments, the biomolecule-binding properties of said mineral micro-particles are at least 1.1-fold, at least 1.2-fold, at least 1.3-fold, at least 1.4-fold, at least 1.5-fold, at least 2-fold, at least 2.5-fold, at least 3-fold, at least 3.5-fold, at least 4-fold or at least 5-fold higher than the biomolecule-binding properties of aluminum phosphate, amorphous aluminum hydroxyphosphate and/or calcium phosphate micro-particles, preferably wherein said biomolecule is an antigen. The ratio of adsorbed biomolecule (e.g. antigen) over aluminum phosphate (mg/g), amorphous aluminum hydroxyphosphate (mg/g) or calcium phosphate (mg/g) micro-particles depends on the combination of the type of modified micro-particle and the nature of the biomolecule (e.g. antigen). For example, the ratio of biomolecule (e.g. antigen) over mineral micro-particle (mg/g) may be at least 3, at least 4, at least 5, at least 6, at least 7, at least 8, at least 9, at least 10, at least 11, at least 12, preferably at least 12.

The mineral micro-particles according to the present invention may have improved physico-chemical properties i.e. increased colloidal stability or reduced aggregation, which may be due to increased electrostatic repulsion between particles; and/or improved biomolecule adsorption and binding, preferably wherein said biomolecule is an antigen.

Furthermore, another aspect of the invention is the use of said mineral micro-particles as taught herein in medicine.

In particular embodiments, medicine may be human and/or veterinary medicine.

In particular embodiments, the mineral micro-particles as taught herein may be used as biomolecules delivery or adsorption systems, preferably wherein said biomolecules delivery system is a vaccine adjuvant.

In particular embodiments, said mineral micro-particles as taught herein may be used in vaccines, preferably as biomolecules delivery systems, more preferably as vaccine adjuvants.

In particular embodiments, said mineral micro-particles as taught herein may be used for manufacturing a vaccine.

Mineral micro-particles which have antigens bound to their surface as taught herein can be used to raise antibodies, such as polyclonal antibodies, in animals. This is achieved by injection of said mineral micro-particles which have antigens bound to their surface into laboratory or farm animals in order to raise high expression levels of antigen-specific antibodies in the serum, which can then be recovered from the animal. Polyclonal antibodies can be recovered directly from serum, while monoclonal antibodies are produced by fusing antibody-secreting spleen cells from immunized mice with immortal myeloma cell to create monoclonal hybridoma cell lines that express the specific antibody in cell culture supernatant.

Therefore, another aspect of the invention is the use of the mineral micro-particles according to the invention, for antibody production.

Mineral micro-particles capable of binding biomolecules and/or contaminants (i.e. arsenic, chromium, nitrate, calcium, radium, uranium, fluoride) can be used as biomolecules adsorption systems, for example in processes of purification, separation, and decontamination of aqueous and other ion-containing solutions (e.g. by functioning as ion exchangers). For example, positively charged mineral micro-particles may be capable of binding albumin, which is negatively charged, and can therefore be used for the removal of albumin from blood samples. In another example, charged mineral micro-particles can be used to selectively enrich acidic or basic proteins in a variety of samples. At an industrial scale, purification, separation, and decontamination is often performed using sorption columns (e.g. ion exchange chromatography).

Accordingly, the mineral micro-particles as taught herein may be used as biomolecules adsorption systems in purification, separation, and decontamination processes.

In particular embodiments, the mineral micro-particles as taught herein may be used for the removal of undesired proteins during blood fractionation.

The present invention is further illustrated in the following non-limiting examples.

EXAMPLES

Experiment No. 1

Formation and Preliminary Characterization of Phytic Acid Precipitates (IP6-M) with $Ca^{2+}$(M=Ca) and $Mg^{2+}$ (M=Mg)

From stock solutions of 200 mM phytic acid (IP6) and 1 M $CaCl_2$ or $MgCl_2$, admixtures were obtained by gradually adding either of $CaCl_2$ or $MgCl_2$ to IP6 such that the final concentrations for $Ca^{2+}$ or $Mg^{2+}$ and IP6 were 50 mM ($M^{2+}$/IP6, 1:1). Precipitates were formed immediately upon addition of the alkaline earth metal salts. After vigorous stirring, the precipitates were pelleted by centrifugation at 12000×g for 30 min. Pellets were rinsed with large volumes of de-ionized water (18 MΩ), such that the final dilution factor of free counter ions was 3000-fold, yielding a theoretical concentration of (50*2)/3000=33 μM for $Cl^-$ ions, for example. Rinsed precipitates were used for physical and chemical analyses.

Particle size and zeta-potential were measured by Dynamic Light Scattering (DLS, Zetasizer Nano ZS, Malvern Instruments) by suspending an aliquot of precipitate in de-ionized water. pH values of the suspensions were recorded. Results in Table 1 show that the particle size of IP6-M is comparable to that of classical adjuvants such as aluminum salts, which is typically comprised between 2 μm and 5 μm. It appears that IP6-Ca particle size, at about 1 μm, is smaller than that of IP6-Mg and that of aluminum salt particles. This feature is of interest as it may answer a current need in the vaccine industry to formulate particulate adjuvants with a particulate size in the 100 to 500 nm range, which have been shown to have enhanced stimulatory properties due to their smaller size. Both particles show negative zeta-potentials also similar to those measured for aluminum hydroxy-phosphate adjuvant particles, which means that these IP6-M particles will be well-suited for the adsorption of positively charged antigens or immunopotentiators.

TABLE 1

Size and zeta-potential values of phytic acid precipitates with calcium (IP6-Ca) and magnesium (IP6-Mg).

| | | pH not adjusted | | pH adjusted | |
|---|---|---|---|---|---|
| Sample | Average particle diameter (nm) | Zeta-potential (mV) | pH | Zeta-potential (mV) | pH |
| IP6-Ca | 992 | −44.5 | 8.50 | −34.8 | 6.94 |
| IP6-Mg | 1875 | −47.4 | 9.15 | −28.8 | 7.09 |

Values are averages of 3 independent measurements. pH values were adjusted by addition of dilute HCl to the suspensions before zeta-potential measurements.

To determine the stoichiometric ratios of phytic acid and $M^{2+}$ ions in the (rinsed) precipitates, Energy Dispersive X-ray scattering (EDXS) analyses were performed. From the spectra (FIGS. 1 and 2), semi-quantitative values of the relative contents in chemical elements can be derived (Table 2). Phytic acid elemental formula is $C_6O_{18}H_{12}P_6$ (fully protonated form) which translates into a C/O/P stoichiometric ratio of 20/60/20 (Table 2, IP6 theo.). Taking the values for Carbon as reference, Table 2 shows that the stoichiometric ratios C/M are 1:1.36 for IP6-Ca and 1:1 for IP6-Mg, respectively.

Given the phytate/M ratios of this analysis, it can be concluded that the stoichiometric ratios of phytate/M are 1:8.14 for IP6-Ca and 1:6 for IP6-Mg, i.e. 6 Mg atoms per phytic acid molecule in IP6-Mg, which corresponds to the theoretical maximum for phytic acid precipitating with divalent cations ($PhyM_6$). In the case of IP6-Ca, higher contents of Ca were recorded (8 Ca atoms per phytic acid molecule in IP6-Ca), which finding may possibly be explained by Calcium phytate precipitating with another anion (denoted "X") to form $PhyCa_8X_2$. This has yet to be corroborated.

As highlighted in the last row of Table 2, the theoretical C/O/P ratio for phytic acid is 20/60/20. When the measured relative amounts of C, O, and P were re-normalized to yield a sum of 100% (IP6 norm.), it appeared for both IP6-Ca and IP6-Mg that O and P were in slight stochiometric excess to C (Table 2). This could indicate the presence of free ortho-phosphate in the batch of IP6 used for this experiment, which might have co-precipitated with IP6-M.

Other stochiometric ratios than the ones observed in the above two experiments may be possible, and is the subject of further investigation. The stoichiometric ratios will depend on the conditions for precipitate formation, such as the relative concentrations and form of reactants, pH, temperature, mode and speed of reactants admixing, thermodynamic stability of initial precipitates etc. Likewise, crystallinity and form of the precipitates may also vary considerably depending on the conditions of reaction.

TABLE 2

Relative elemental contents in IP6-M precipitates as measured with EDXS.

|  | C | O | P | Ca or Mg | Na |
|---|---|---|---|---|---|
| IP6-Ca | 14 ± 0.5 | 47 ± 0.5 | 17 ± 0.3 | 19 ± 1.0 | 2.5 ± 0.3 |
| IP6 norm. | 17 | 61 | 22 |  |  |
| IP6-Mg | 13 ± 0.2 | 51 ± 0.7 | 18 ± 0.8 | 13 ± 0.2 | 4.2 ± 0.1 |
| IP6 norm. | 16 | 62 | 22 |  |  |
| IP6 theo. | 20 | 60 | 20 |  |  |

Experiment No. 2

Formation and Preliminary Characterization of Phytic Acid Precipitates with Poly-L-Lysine.

From stock solutions of 200 mM phytic acid (IP6) and 100 µg/mL of low molecular weight poly-L-lysine (1000 to 5000 Da), an admixture was obtained by gradually adding poly-L-lysine to IP6 such that the final concentration for phytic acid was 100 mM and that of poly-L-lysine was 20 mM (based on average Mw of 3000 Da). Precipitates were formed immediately upon addition of poly-L-lysine, however the particulate matter formed could not be pelleted by centrifugation, indicating a material density close to that of water. A sample of this material was diluted 10-fold for particle size and zeta-potential measurement by Dynamic Light Scattering (DLS, Zetasizer Nano ZS, Malvern Instruments). Results in Table 2 show that the particle size of IP6-poly-L-lysine is about 1.1 µm and the zeta-potential −29 mV in these experimental conditions. Further dilution with de-ionized water to 100-fold resulted in an increase in optical density (visible with naked eye), indicative of further particle formation. The size of particles increased to 2.9 µm and the zeta potential did not change markedly.

The stability of the particles formed by complexation between phytic acid and poly-L-lysine (low Mw) appears to be marginal, as phase separation was observed several hours after formation of the colloid. Re-mixing of the phases yielded the colloid.

TABLE 3

Size and zeta-potential values of phytic acid percipitates with poly-L-lysine (IP6-pLLys).

| Sample | Average particle diameter (nm) | pH not adjusted Zeta-potential (Mv) |
|---|---|---|
| IP6-pLLys (10-fold) | 1100 | −29.0 |
| IP6-pLLys (100-fold) | 2900 | −25.0 |

Values are averages of 3 independent measurments.

The invention claimed is:

1. Mineral microparticles comprising one or more salts of phytic acid (IP6), the IP6 salts comprising organic polycations and divalent alkaline earth metal ions $M^{2+}$ selected from $Ca^{2+}$, $Mg^{2+}$ or mixtures thereof,
    wherein the microparticles have a nominal size of at least 0.5 µm and at most 2 µm, and wherein the stoichiometric ratio of phytic acid to the divalent alkaline earth metal ions is 1:6 to 1:8, and
    wherein an antigen is adsorbed on a surface of at least a portion of the microparticles.

2. The mineral microparticles according to claim 1, wherein calcium phytate is present and has a nominal zeta-potential when measured at pH 7.0 in distilled water of at least −34 mV.

3. The mineral microparticles according to claim 1, wherein the mineral microparticles are present in a biomolecules delivery system and the biomolecules delivery system is a vaccine adjuvant.

4. A vaccine adjuvant composition comprising mineral micro particles,
    wherein the mineral microparticles comprise one of more salts of phytic acid (IP6), the IP6 salts comprising organic polycations and divalent alkaline earth metal ions $M^{2+}$ selected from $Ca^{2+}$, $Mg^{2+}$ or mixtures thereof,
    wherein the vaccine adjuvant composition is combined with an antigen to form a vaccine composition,
    wherein the microparticles have a size of at least 0.5 µm and at most 2 µm, and
    wherein an antigen is adsorbed on a surface of at least a portion of the microparticles.

5. The adjuvant composition according to claim 4 wherein the mineral microparticles have a size of between 0.5 to 1 µm.

6. A antigen delivery or adsorption system comprising the mineral microparticles according to claim 1.

7. The antigen delivery or adsorption system according to claim 6, wherein the antigen delivery system is a vaccine adjuvant.

8. The mineral microparticles according to claim 1, wherein the organic polycation is selected from the group consisting of (poly)lysine and poly-D-glucosamine.

* * * * *